(12) United States Patent
Andrews et al.

(10) Patent No.: US 9,086,424 B2
(45) Date of Patent: Jul. 21, 2015

(54) METHOD FOR DETERMINING EQUIVALENT THERMAL CONDITIONS BETWEEN LIQUID CHROMATOGRAPHY SYSTEMS

(75) Inventors: Richard W. Andrews, Rehoboth, MA (US); Peyton C. Beals, Wreatham, MA (US)

(73) Assignee: Waters Technologies Corporation, Milford, MA (US)

( * ) Notice: Subject to any disclaimer, the term of this patent is extended or adjusted under 35 U.S.C. 154(b) by 478 days.

(21) Appl. No.: 13/519,712

(22) PCT Filed: Jan. 21, 2011

(86) PCT No.: PCT/US2011/021999
§ 371 (c)(1),
(2), (4) Date: Jun. 28, 2012

(87) PCT Pub. No.: WO2011/091224
PCT Pub. Date: Jul. 28, 2011

(65) Prior Publication Data
US 2012/0285223 A1  Nov. 15, 2012

Related U.S. Application Data

(60) Provisional application No. 61/297,984, filed on Jan. 25, 2010.

(51) Int. Cl.
*G01N 30/02* (2006.01)
*G01N 30/86* (2006.01)
*B01D 15/42* (2006.01)
*G01N 30/30* (2006.01)

(52) U.S. Cl.
CPC .......... *G01N 30/8672* (2013.01); *B01D 15/424* (2013.01); *G01N 2030/3007* (2013.01)

(58) Field of Classification Search
CPC ................................ B01D 15/10; B01D 15/22
USPC .......................................................... 73/61.53
See application file for complete search history.

(56) References Cited

U.S. PATENT DOCUMENTS

| 4,802,102 A | 1/1989 | Lacey |
| 5,568,400 A | 10/1996 | Stark et al. |

(Continued)

OTHER PUBLICATIONS

International Search Report for counterpart international patent application No. PCT/2011/021999 dated May 9, 2011; 3 pages.

*Primary Examiner* — Hezron E Williams
*Assistant Examiner* — Mark A Shabman
(74) *Attorney, Agent, or Firm* — Schmeiser, Olsen & Watts LLP; William G. Guerin

(57) ABSTRACT

Described is a method of transferring a chromatographic method between liquid chromatography (LC) systems. The method is based on a determination of an isoretention temperature at which two solutes co-elute. The method enables separations to be performed using different LC systems with reproducible and equivalent results. For example, the method allows for a chromatography method developed for HPLC to be more readily transferred to a UPLC system and for a chromatography method developed for a UPLC system to be more readily transferred to a HPLC system. The method addresses LC systems having column ovens of different design in which the internal column temperatures are not equal although the operating temperatures of the column ovens may be accurately controlled to equal values. The retention behavior and resolution of different LC systems is caused to be substantially the same so that equivalent separation results are obtained.

19 Claims, 4 Drawing Sheets

(56) References Cited

U.S. PATENT DOCUMENTS

| | | |
|---|---|---|
| 5,970,425 A | 10/1999 | Ono et al. |
| 6,153,438 A * | 11/2000 | Blumberg et al. ............ 436/161 |
| 6,357,277 B1 * | 3/2002 | Pigozzo et al. .............. 73/23.22 |
| 6,494,078 B1 | 12/2002 | Klee |
| 6,915,227 B2 | 7/2005 | Quimby et al. |

* cited by examiner

METHOD FOR DETERMINING EQUIVALENT THERMAL CONDITIONS BETWEEN LIQUID CHROMATOGRAPHY SYSTEMS

RELATED APPLICATION

This application claims the benefit of the earlier filing date of U.S. Provisional Patent Application Ser. No. 61/297,984, filed Jan. 25, 2010 and titled "Equivalent Thermal Conditions in Different HPLC and UHPLC Systems for Transfer of Chromatography Methods," the entirety of which is incorporated herein by reference.

FIELD OF THE INVENTION

The invention relates generally to a method for determining equivalent thermal conditions between or among chromatographic systems. More particularly, the invention relates to control of column temperatures to obtain equivalent elution of common samples regardless of the particular chromatographic system used to perform a separation.

BACKGROUND

The control of column temperature is important to the resolving efficiency of a liquid-chromatography (LC) column regardless of whether the system is designed to operate isothermally or by temperature programmed analysis. Column temperature control is commonly achieved by heating of the column, for example, in a convection oven or in an oven with still air.

Some chromatographic systems utilize a column heater to control column temperature. For example, the column may be located in a temperature controlled chamber. The temperature of the fluid mixture or mobile phase provided to the column may not be constant, especially for long (e.g., multi-hour) chromatographic runs where the variations in room temperature are significant. Temperature variations can adversely impact the accuracy of the chromatographic analysis. In some systems, a device is used to pre-heat the mobile phase before the mobile phase is injected into the column to reduce column inlet fluid temperature fluctuations.

The design of the column oven is typically different for different chromatographic systems. The particular design used is based, in part, on the requirement to achieve stable retention times and separation metrics (e.g., selectivity, peak shape and column efficiency) despite variations in the ambient temperature; however, variances in the designs can lead to differences in chromatographic results when separations of identical samples are performed on different LC systems.

SUMMARY

In one aspect, the invention features a method of transferring a chromatographic method between LC systems. The method includes determining an isoretention temperature of a first LC system at which a first solute and a second solute in a mobile phase of the first LC system co-elute from a column. An isoretention temperature of a second LC system at which the first solute and the second solute in a mobile phase of the second LC system co-elute from a column is determined. A column offset temperature for transferring a chromatographic method between the first and second LC systems is determined based on the difference in the isoretention temperatures of the first and second LC systems.

In another aspect, the invention features a method of transferring a chromatographic method between LC systems. According to the method, for a plurality of solute pairs each having a first solute and a second solute, a determination of an isoretention temperature of a first LC system at which the first solute and the second solute in a mobile phase of the first LC system co-elute from a column is made. An isoretention temperature of a second LC system at which the first solute and the second solute in a mobile phase of the second LC system co-elute from a column is determined for each of the solute pairs. A column offset temperature for transferring a chromatographic method between the first and second LC systems based on the difference in a respective pair of isoretention temperatures of the first and second LC systems is determined for each solute pair.

In another aspect, the invention features a method of transferring a chromatographic method between LC systems. According to the method, a van't Hoff functional relationship for a first solute in a mobile phase for a plurality of column temperatures for a first LC system is determined and a van't Hoff functional relationship for a second solute in a mobile phase for a plurality of column temperatures for the first LC system is determined. An isoretention temperature of the first LC system for the first and second solutes is determined as a temperature at which a retention factor of each of the van't Hoff functional relationships of the two solutes in the first LC system are equal. A van't Hoff functional relationship for the first solute in a mobile phase for a plurality of column temperatures for a second LC system is determined and a van't Hoff functional relationship for the second solute in a mobile phase for a plurality of column temperatures for the second LC system is determined. An isoretention temperature of the second LC system for the first and second solutes is determined as a temperature at which a retention factor of each of the van't Hoff functional relationships of the two solutes in the second LC system are equal. A column offset temperature for transferring a chromatographic method between the first and second LC systems is determined based on the difference in the isoretention temperatures of the first and second LC systems.

In another aspect, the invention features method of transferring a chromatographic method between LC systems. According to the method, for each solute in a plurality of first solutes, a van't Hoff functional relationship for the first solute in a mobile phase for a plurality of column temperatures for a first LC system is determined and, for each solute in a plurality of second solutes, a van't Hoff functional relationship for the second solute in a mobile phase for a plurality of column temperatures for the first LC system is determined. For a plurality of solute pairs each including one of the first solutes and one of the second solutes, an isoretention temperature of the first LC system is determined as a temperature at which a retention factor of the van't Hoff functional relationships of the respective first and second solutes in the first LC system are equal.

For each of the first solutes, a van't Hoff functional relationship for the first solute in a mobile phase for a plurality of column temperatures for a second LC system is determined and, for each of the second solutes, a van't Hoff functional relationship for the second solute in a mobile phase for a plurality of column temperatures for the second LC system is determined. For each of the solute pairs, an isoretention temperature of the second LC system is determined as a temperature at which the retention factor of the van't Hoff functional relationships of the first and second solutes in the second LC system are equal. For each of the solute pairs, a column offset temperature for transferring a chromatographic method between the first and second LC systems is determined based on a difference in a respective pair of isoretention temperatures of the first and second LC systems.

In still another aspect, the invention features a sample for determining an isoretention temperature of a LC system. The sample includes a solvent and a solute pair. The solute pair includes two solutes dissolved in the solvent. The solute pair is predetermined to have a temperature at which the two solutes co-elute from a column of a LC system.

In yet another aspect, the invention features a sample for determining isoretention temperatures of a LC system. The sample includes a solvent and a plurality of solute pairs. Each of the solute pairs includes two solutes dissolved in the solvent and has a temperature at which the two solutes co-elute from a column of a LC system. The temperature for co-elution for each solute pair is different from the temperatures for co-elution for each of the other solute pairs.

BRIEF DESCRIPTION OF THE DRAWINGS

The above and further advantages of this invention may be better understood by referring to the following description in conjunction with the accompanying drawings, in which like numerals indicate like structural elements and features in the various figures. For clarity, not every element may be labeled in every figure. The drawings are not necessarily to scale, emphasis instead being placed upon illustrating the principles of the invention.

DETAILED DESCRIPTION

Figure 1:
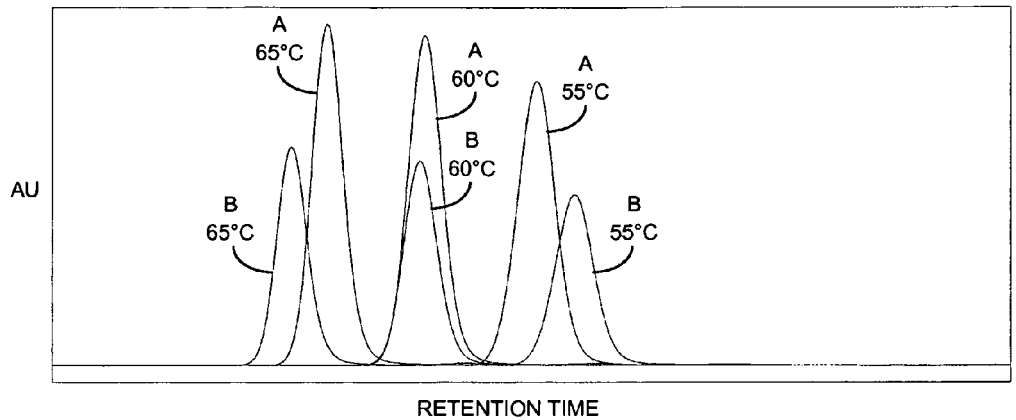
FIG. 1 graphically illustrates the temperature-dependent retention times for a separation of two solutes in a LC system.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The following discussion will make reference to exemplary embodiments as shown in the accompanying drawings. While various embodiments and examples are described, it is not intended that the invention be limited to such embodiments. On the contrary, the invention contemplates various alternatives, modifications and equivalents, as will be appreciated by those of skill in the art. Those of ordinary skill will recognize additional implementations, modifications and embodiments, as well as other fields of use, which are within the scope of the present disclosure as described herein.

A column for LC analysis is usually in the form of a packed bed or is an open tubular column. The column contains a stationary phase, that is, a material for which the components to be separated have varying affinities. A mobile phase of the chromatographic process is generally a solvent or mixture of solvents into which the sample to be analyzed is injected. The mobile phase enters the column and the sample adsorbs onto the stationary phase. The solvent or solvent mixture is not adsorbed on the stationary phase and instead passes through the column. It should be noted that the word "column" as used herein generally means any device or component that contains the stationary phase and is not intended to limit embodiments to columns of any particular construction, number configuration, width or diameter. For example, in some embodiments the column can be formed according to a variety of geometries on a microfluidic substrate.

In some binary solvent delivery systems a first pump draws a first solvent from a tank and supplies the first solvent at a desired flow velocity and pressure to a T-shaped piping connector. A second pump draws a second solvent from a second tank and supplies the second solvent at a desired flow velocity and pressure to the T-shaped piping connector. The solvents are blended at the connector to achieve a solvent mixture having desired properties. The flow rate of each solvent can be adjusted to vary the composition of the solvent mixture over time. A variation in the solvent mixture over time is referred to as a solvent or compositional gradient.

As the mobile phase passes through the column, different components in the mobile phase adsorb to the stationary phase to varying degrees. Components with a strong attraction to the stationary phase move more slowly through the column than components with a weak attraction. Thus the components are separated according to the different speeds of movement through the column and elute from the column at different times. The component with the least affinity for the stationary phase elutes first, while the component with the greatest affinity for the stationary phase elutes last. A detector analyzes the emerging stream by measuring a property that is related to the concentration and characteristic of chemical composition. By way of specific examples, the measured property can be the refractive index or ultra-violet absorption.

Some chromatographic systems utilize a column heater to control column temperature. For example, the column may be located in a temperature controlled chamber such as a convection oven or a chamber employing resistance heating. The control of column temperature is important to the resolving efficiency of a liquid-chromatography column, whether the system is designed to operate isothermally or by temperature programmed analysis. In particular, the retention time and peak shape vary in response to changes in the column temperature.

If the temperature of the mobile phase supplied to the column is not constant, for example, for long (e.g., multi-hour) chromatographic runs where the variations in room temperature are significant, the accuracy of the chromatographic analysis can degrade. A device to pre-heat the mobile phase is sometimes used to reduce temperature fluctuations at the column inlet.

Traditional high-performance liquid chromatography (HPLC) techniques have typically utilized analytical columns constructed from stainless-steel tubing having an inner bore diameter of 4.6 mm and lengths in a range of about 5 cm to about 25 cm. To complete an analytical column for a HPLC instrument, a fritted end-fitting is typically attached to a piece of tubing, and the tubing is then packed with particles such as silica-based particles that are functionalized with a variety of functional moieties.

The flow rate of the mobile phase is important for achieving optimal separation efficiency using the completed column. For a 4.6 mm diameter column packed with 5 μm diameter particles, a desirable flow rate is typically between about 1 mL/min and about 2 mL/min. To maintain separation efficiency, it is also desirable to minimize the presence of unswept dead volume in the plumbing of the HPLC instrument.

In a HPLC instrument, an injector is typically used to inject a sample into a flowing mobile phase as a discrete fluidic plug. Dispersion of a plug band traveling to and/or from the column reduces the efficiency of the chromatographic system. For example, in a chromatographic system using 4.6 mm column tubing and a mobile phase flowing at 1 mL/min to 2 mL/min, tubing having an outer diameter of 1/16 inch and an inner diameter of about 0.010 inch is typically used to plumb connections between the various HPLC components (e.g., pump, injector, column and detector). For these flow rates and tubing dimensions, it is relatively easy to machine port details to tolerances that ensure minimal band broadening at tubing interfaces.

A desire to reduce the consumption of the mobile phase solvent has motivated a trend to reduce the inner diameter of the column. Thus different scales of chromatography are now commonly practiced. These are typically defined according to Table 1 where "ID" indicates inner diameter.

TABLE 1

| HPLC Scale | Column ID | Typical Flow range |
| --- | --- | --- |
| Analytical | 4.6 mm | 1's mL/min |
| Microbore/UPLC | 1-2 mm | 100's µL/min |

Microbore HPLC is often practiced with equipment similar to that used for analytical scale HPLC with minor modifications. Although additional care is generally taken when making fittings, microbore HPLC typically requires an operating skill level similar to that of analytical scale HPLC.

Ultra performance liquid chromatography (UPLC) is generally performed with traditional microbore columns (2.1 mm ID); however, packing material with particle diameters less than 2 µm are commonly used. The smaller particle sizes result in higher column efficiency and enable operation with a higher separation speed. Advantageously, the smaller column dimensions permit lower volumetric flow rates while reducing run time and yielding a more efficient separation with improved resolution.

While a primary motivation to replace analytical-scale HPLC with microbore-scale HPLC and UPLC is often a desire to reduce solvent consumption, the main benefits of such transfers are improvements in speed of analysis, chromatographic resolution and sensitivity. Consequently, transferring a method from a HPLC system to a UPLC system should ensure that the selectivity of the separation is preserved while speed, resolution and sensitivity are enhanced. The selectivity of the separation is described by the relative retention times of the peaks within the chromatogram or by the separation factor $\alpha$ between adjacent peaks. The selectivity is primarily determined by the composition of the mobile phase, the specific stationary phase bonded to the column and the internal temperature of the column. Adjustment of flow rates and gradient composition to preserve the selectivity is principally determined by the geometry of the columns, the relative particle diameters of the columns and the system volumes of the chromatographs.

The role of column temperature in the control of retention times and the selectivity of separations is recognized as an important factor in performing reproducible separations. A principal aspect to performing reproducible separations is the ability to transfer a chromatographic method between different chromatographic systems. It may be desirable to transfer a method from a HPLC system to a UPLC system or from a UPLC system to a HPLC system. Alternatively, it may be desirable to transfer to another chromatographic system having a different column and/or different column chemistry.

Different chromatographic systems typically incorporate column ovens of different design, in part, to ensure that retention times and separation metrics (e.g., selectivity, peak shape and column efficiency) remain stable while the ambient temperature varies. A common assumption is that the oven temperature and the average internal column temperature are the same. The characterization of a column heater (or cooler) can be performed by measuring the temperature of the column heater at a specified location with a calibrated thermometer or temperature probe; however, this technique does not accurately indicate the internal temperature of the column under chromatographic conditions. In particular, column heaters or coolers operating according to different design principles frequently exhibit different retention behavior when set to the same nominal temperature even if both column heaters provide the same temperature accuracy when measured by an external thermometer.

In UPLC systems, the use of particles smaller than 2 µm leads to significant frictional heating as a result of the pressure-volume work done on the column. Additionally, it is important that the UPLC column be operated in an oven which does not circulate the heating fluid (e.g., air) in order to preserve the separation efficiency. When UPLC columns are operated in column ovens with convective circulation of air, radial thermal gradients are induced within the column. The radial thermal gradients degrade the efficiency of the separation and can lead to split peaks for single components. Because convection ovens degrade the separation efficiency of UPLC columns, the effectiveness of devices used to preheat the mobile phase become significant in UPLC. In HPLC, the absence of significant frictional heating (smaller column backpressure) permits the use of convection ovens for column heating and the performance of inlet preheating is less critical to column temperature control.

Consequently, the assumption that the oven set temperature and the average internal column temperature are the same is generally invalid, especially when the column ovens may differ in their operating principles and efficacy of the inlet preheater. The resulting differences in the internal column temperatures can result in differences in retention and resolution that can compromise the equivalency of test results.

In various embodiments, the method of the invention enables separations to be performed using different chromatography systems with reproducible and equivalent results. For example, the method allows for a chromatography method developed for HPLC to be more readily transferred to a UPLC system and for a chromatography method developed for a UPLC system to be more readily transferred to a HPLC system. The method accommodates column ovens of different design in which the internal column temperatures are not equal although the operating temperatures of the column ovens may be accurately controlled to equal values. The method causes the retention behavior and resolution of different chromatography systems to be substantially the same, resulting in an equivalency of separation results.

Although the embodiments described below relate primarily to control of column temperature by column ovens or heaters, it should be recognized that other embodiments according to the principles of the invention are based on control of the temperature of a column by a cooler or by a temperature control system capable of both heating and cooling a column.

The effect of column temperature on chromatographic measurements is often based on an analysis of van't Hoff plots as is known in the art. One assumption in the generation of van't Hoff plots is that the temperature which controls the partitioning of a solute between the stationary and mobile phases is the set temperature of the column oven. In chromatographic systems, the temperature varies with location within the column. At the column inlet, the primary effect on the temperature is the temperature of the incoming mobile phase which is heated either passively with a heat exchanger connected to the column oven or actively with a separately controlled heat exchanger. At the column outlet, the principal source of heat is based on frictional heating occurring within the column. As particle size decreases from a typical 5 μm particle in conventional HPLC to sub 2 μm in UPLC, the significance of frictional heating associated with higher backpressures increases.

When column backpressures are low the contribution of frictional heating is less significant. Under such conditions, the mechanism of heat transfer within the column oven leads to significant differences in the effective temperature of the column. Various column ovens employ forced convection of heated or cooled air, circulating water jackets and, in some applications, are based on passive heat transfer in an oven with no active air circulation. Each design configuration typically yields linear van't Hoff plots and precise control of retention time. Moreover, each design configuration can provide an accurate temperature at a selected location within the column oven where the temperature is measured with a calibrated thermometer such as a thermocouple or thermistor. However, retention factors typically differ among column ovens especially when the design principles are not the same although identical columns and premixed mobile phases may be used.

Equation (1) is one form of the van't Hoff equation where K is the equilibrium constant for partitioning, k' is the retention factor and θ is the phase ratio.

$$ln(K) = ln(k') - ln(\theta). \quad (1)$$

The right side of the equation can be rewritten as follows:

$$ln(k') - ln(\theta) = -1/RT^* \Delta G° \quad (2)$$

where R is the gas constant, T is the absolute temperature in Kelvin and $\Delta G°$ is the Gibbs free energy. Equations (1) and (2) can be used to derive the following relationship:

$$ln(k') = -[\Delta G°/R]^*(1/T) + ln(\theta). \quad (3)$$

The van't Hoff functional relationship provided in equation (3) can be graphically represented for a particular solute as a plot of ln(k') as a function of inverse temperature T. In general such van't Hoff plots are linear. Variations from linearity are typically associated with poor heat transfer at higher temperatures and higher flow rates, or with frictional heating at lower temperatures where a high solvent viscosity results in a significant pressure drop across the analytical column.

If the van't Hoff plots for the components of a mixture are parallel or do not intersect in the temperature range of an LC system, adjustment of the set temperature of the column oven is straightforward because the order of elution of the components does not change and relative retention metrics are typically well preserved. In that case, the temperature is incremented to ensure that the retention factor k' is held constant for each of the critical components of the sample.

In contrast, when the van't Hoff plots intersect, the components co-elute at the temperature corresponding to the intersection point, that is, the components co-elute at an "isoretention temperature." In addition, the order of elution reverses as the column temperature transitions through the isoretention temperature. This can result in misidentified peaks as well as incomplete separations of critical peak pairs.

By way of example, FIG. 1 shows how the retention times for two solutes A and B decrease with increasing temperature. In this example, the isoretention temperature is slightly less than 60° C. Solute A elutes before a solute B for temperatures less than the isoretention temperature while solute A elutes after the second solute B for temperatures greater than the isoretention temperature. The two solutes A and B co-elute when the column temperature is maintained at the isoretention temperature. The possibility of a reversal of the order of elution, or "peak order reversal", with a change in column temperature can be problematic for unknown peaks within a chromatogram especially when the set temperature of the column is nearly equal to the isoretention temperature for the corresponding solutes.

At the intersection point of two van't Hoff plots, the separation factor α, defined as the ratio $(k_B'/k_A')$ of the respective retention factors, is one and the phase ratio θ is eliminated. Thus equation (3) can be expressed as $$T_{iso} = [\Delta H°_B - \Delta H°_A]/[\Delta S°_B - \Delta S°_A] + \phi(t) \quad (4)$$

where $\Delta H°_A$ and $\Delta H°_B$ are the enthalpy changes associated with the partitioning of compounds A and B, respectively, and $\Delta S°_A$ and $\Delta S°_B$ are the entropy changes associated with the partitioning of compounds A and B, respectively. $\phi(t)$ is an error term that incorporates all of the non-equilibrium contributions to the isoretention temperature $T_{iso}$. Ideally, $\phi(t)$ has a small value (e.g., less than 1° C.) and does not have a strong dependence on temperature. The isoretention temperature $T_{iso}$ is a property of the interaction of the solutes with the stationary and mobile phases and equation (4) includes the error term associated with the measurement. The isoretention temperature can be determined by plotting the two van't Hoff plots and determining the intersection point. Alternatively, the isoretention temperature can be established by determining the temperature of co-elution, that is, the temperature at which the separation factor α has a value of one. In many instances, the second approach is a more efficient and convenient approach.

If frictional heating does not contribute significantly to the internal column temperatures, separations performed for two different chromatography systems each using the same type of column, same solute pair and same mobile phase conditions can be used to relate the effective column temperatures. In particular, the difference in the isoretention temperatures is a measure of the difference in the average internal column temperatures, or effective column temperatures, for two LC systems set to the same column temperature.

Figure 2:
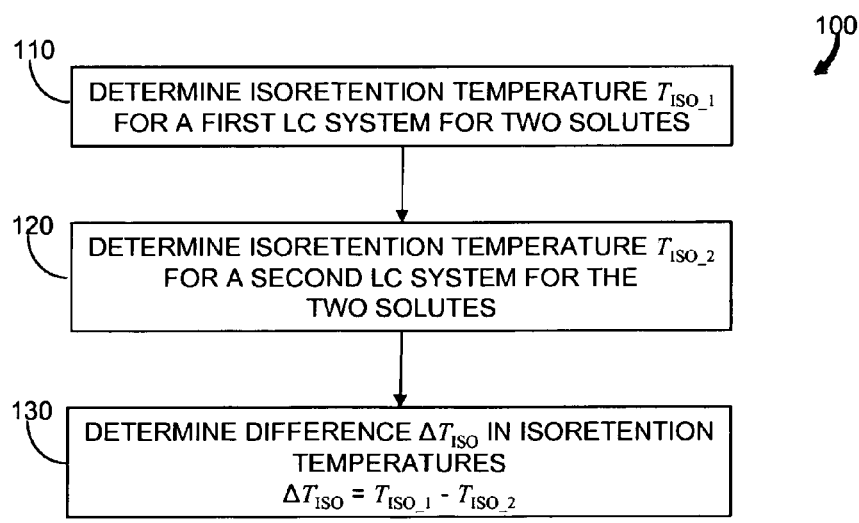
FIG. 2 is a flowchart representation of an embodiment of a method for determining a difference in average column temperatures for two chromatographic systems according to the invention.

FIG. 2 shows a flowchart representation of an embodiment of a method 100 for determining a difference in isoretention column temperatures for two chromatographic systems according to the invention. The difference in the average column temperature can be used to transfer a chromatography method between two LC systems that differ in design principle and implementation.

A first LC system is used to determine (step 110) an isoretention temperature $T_{ISO\_1}$ for two solutes. A second LC system employing the same type of column and mobile phase conditions is used to determine (step 120) an isoretention temperature $T_{ISO\_2}$ for the same two solutes. The difference in the isoretention temperatures $\Delta T_{ISO}$ of the two LC systems is determined (step 130) and can subsequently be used to transfer a chromatography method from one of the LC systems to the other LC system. In particular, if the isoretention temperature $T_{ISO\_1}$ of the first LC system is greater, to transfer a chromatographic method from the first system to the second LC system, the column temperature for the second LC system is set to a value that is less than the column temperature previously used for the chromatography method of the first LC system by the difference $\Delta T_{ISO}$. Conversely, if the isoretention temperature $T_{ISO\_1}$ of the first LC system is less, to transfer a chromatographic method from the first LC system to the second LC system, the column temperature for the second LC system is set to a value that is greater than the column temperature for the chromatography method of the first LC system by the difference $\Delta T_{ISO}$.

To accurately transfer chromatography methods between LC systems, it is preferable to ensure that the column temperature set for a separation is not significantly different from the determined isoretention temperatures. Thus the ability to transfer chromatographic methods may be limited to a small column temperature range (e.g., within ±10° C.).

For example, to transfer a separation carried out on a first LC system with a set temperature of 65° C. to a second LC system, it is desirable to choose a solute pair which has an isoretention temperature that is close to 65° C. This ensures that the differences in the performance of the inlet preheaters of both systems are accurately modeled. By way of example, FIG. 3 (described in more detail below) suggests that the isoretention temperature of 63° C. for the solutes TNT and 4-amino DNT (63° C.) is a suitable choice.

To expand the range of temperatures for transferring chromatography methods, steps 110 to 130 of the method 100 can be repeated using different pairs of solutes. Thus isoretention temperatures $T_{ISO\_1}$ and $T_{ISO\_2}$ can be determined for each LC system for a number of pairs of solutes and the difference in the isoretention temperatures for a common pair of solutes can be used to transfer a chromatography method from one LC system to the other for a limited range of temperatures (e.g., ±10° C.) about the determined isoretention temperature. Preferably, the selections of the solute pairs used to determine isoretention temperatures are made to obtain isoretention temperatures that span a large temperature range to thereby reduce limitations on temperatures than can be utilized in the transfer of chromatography methods between LC systems. In some embodiments, each solute pair is a separate injection into the LC system. In alternative embodiments, at least two solute pairs are present in at least one of the injections thereby reducing the time and effort necessary to obtain the distribution of isoretention temperatures for the LC system.

Figure 3:
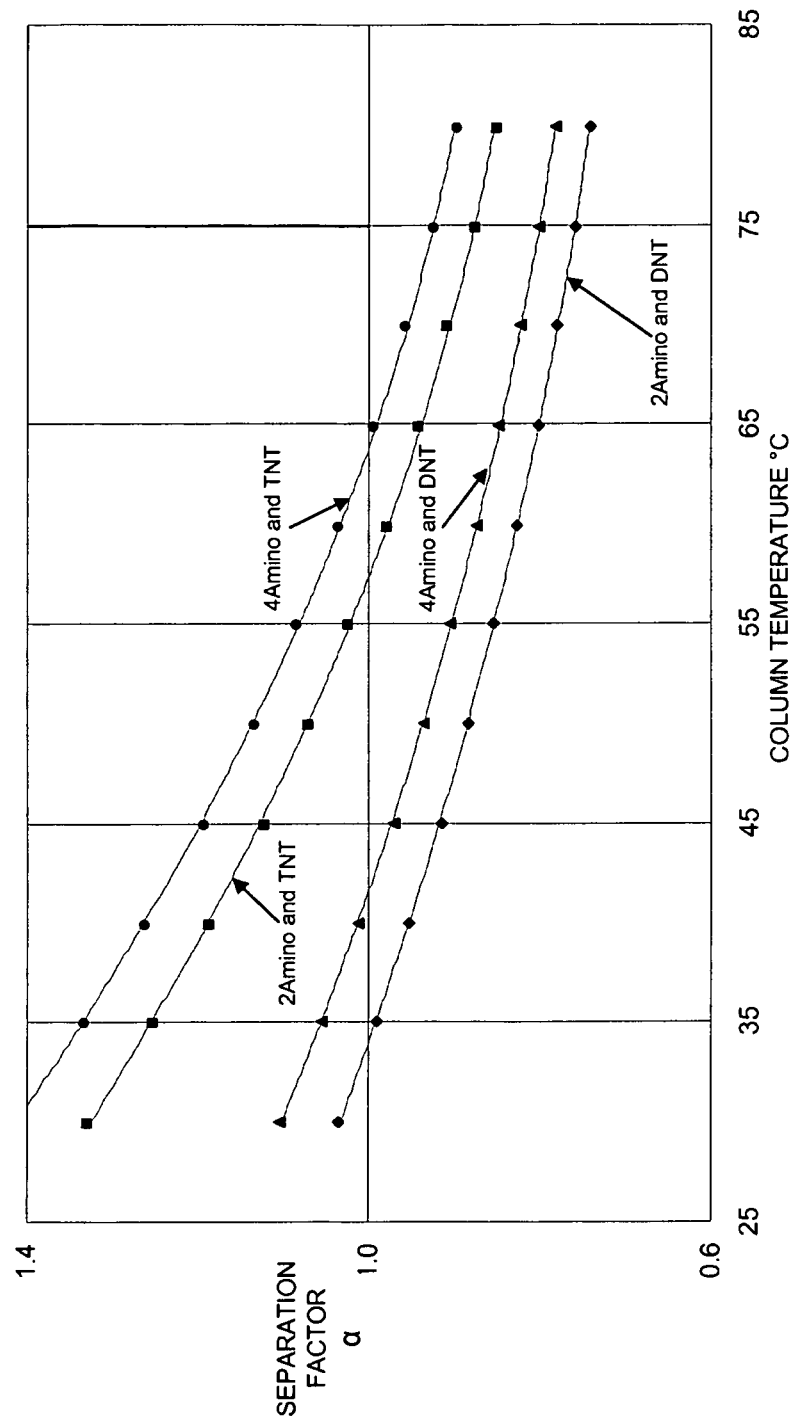
FIG. 3 graphically illustrates the separation factor as a function of column temperature for four solute pairs.

Some solutes may be paired with more than one other solute. For example, solute A and solute B may be used to determine one isoretention temperature while solute A and solute C can be used to determine a different isoretention temperature. FIG. 3 graphically illustrates the separation factor $\alpha$ as a function of column temperature for four solute pairs selected from a set of four nitrotoluene standards: 2,4,6-trinitrotoluene, 2,4-dinitrotoluene, 2-amino,4,6-dinitrotoluene and 4-amino,2,6-dinitrotoluene ("TNT", "DNT", "2Amino" and "4Amino", respectively). The isoretention temperature for each solute pair is determined as the temperature at which the separation factor $\alpha$ for the solute pair has a value of one. The relatively small change in the slope of the plots between adjacent data samples allows linear interpolation to be applied to determine the isoretention temperatures without introducing substantial error. From the plots, the isoretention temperatures for 2Amino and DNT, 4Amino and DNT, 2Amino and TNT, and 4Amino and TNT for the subject LC system are determined to be 31.4° C., 41.7° C., 57.5° C. and 63.9° C., respectively. Thus the four nitrotoluene standards cover a significant portion of the column temperature range of many HPLC and UPLC systems.

To transfer from the LC system associated with the data in FIG. 3 to another LC system (or from another LC system to the subject LC system), the isoretention temperatures of the other LC system are similarly determined, and the matched isoretention temperatures (i.e., isoretention temperatures for the same solute pair) of the two LC systems that are closest in value to the desired column temperature for the separation to be performed are differenced to determine the appropriate column offset temperature for performing the separation.

Other solutes can be used to generate a number of isoretention temperatures for LC systems. In some instances, the particular solutes employed may exhibit more complex behaviors. Consequently, various alternative techniques for peak identity tracking may be preferred so that the user can determine the retention time of each solute at each temperature. For example, manipulation of the relative amounts of each solute may be desired as well as the use of multiwavelength detection or spectroscopic measurements to achieve a finer peak tracking resolution.

Figure 4:
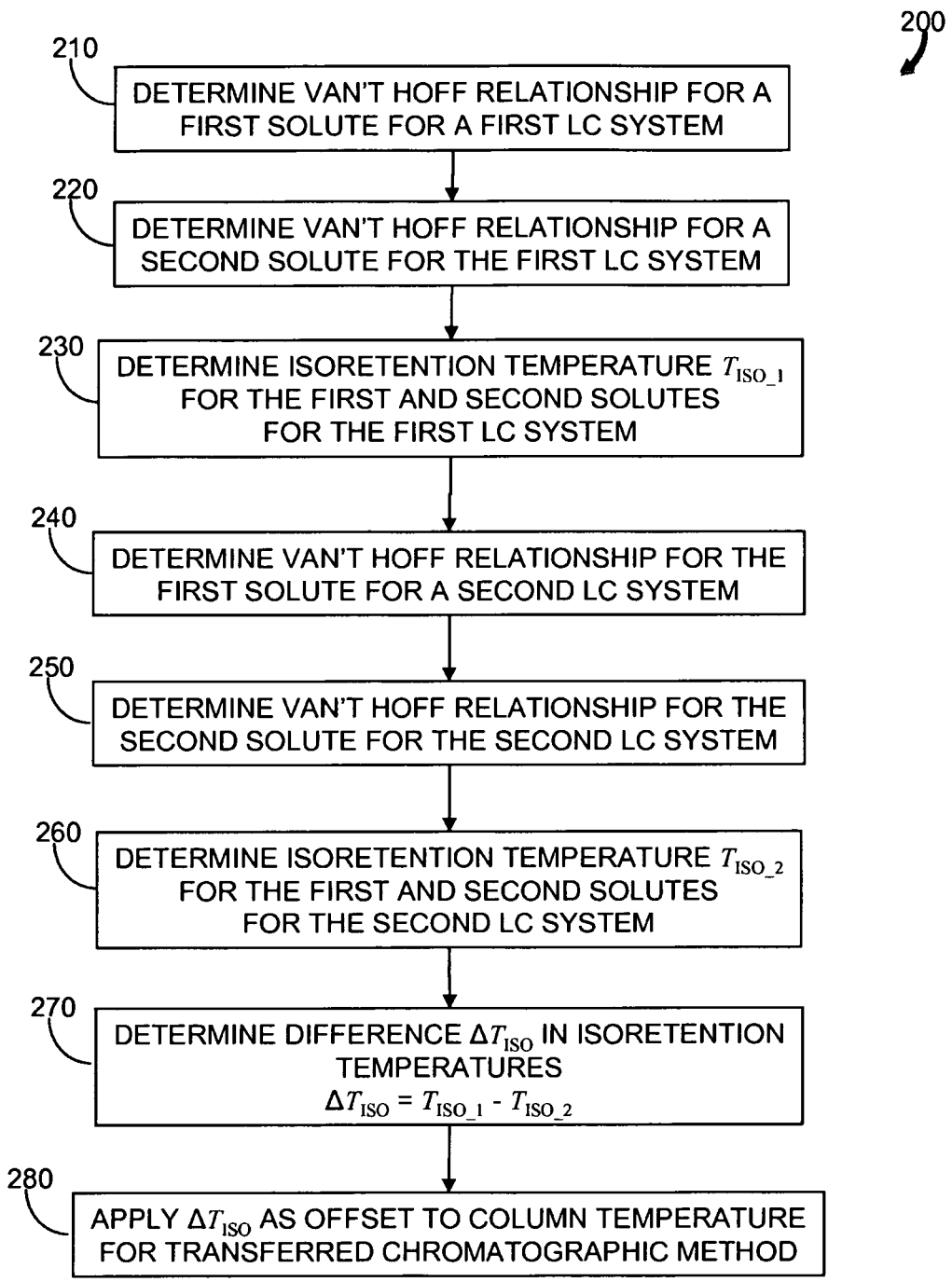
FIG. 4 is a flowchart representation of another embodiment of a method for determining a difference in average column temperatures for two chromatographic systems according to the invention.

FIG. 4 shows a flowchart representation of another embodiment of a method 200 for determining a difference in average column temperatures for two chromatographic systems according to the invention. Accordingly, a first LC system is used to determine (step 210) a van't Hoff functional relationship for a solute. More particularly, the natural log of the retention factor k' is determined as a function of inverse column temperature T. Similarly, the first LC system is used to determine (step 220) the van't Hoff functional relationship of a second solute using the same column and mobile phase.

Using the two van't Hoff functional relationships, an isoretention temperature $T_{ISO\_1}$ for the two solutes is determined (step 230). The two van't Hoff functional relationships may be plotted or graphically displayed and the isoretention temperature $T_{ISO\_1}$ determined by identifying the column temperature at the intersection of the two plots.

A second LC system is used to determine (steps 240 and step 250) the van't Hoff functional relationships for the same two solutes used with the first LC system. An isoretention temperature $T_{ISO\_2}$ is determined (step 260) from the two van't Hoff functional relationships for the second LC system. The difference $\Delta T_{ISO}$ of the isoretention temperatures $T_{ISO\_1}$ and $T_{ISO\_2}$ of the first and second LC systems is determined (step 270) and can be used as the column offset temperature to adjust for the transfer of a chromatographic method between the two LC systems as described above. In particular, the difference $\Delta T_{ISO}$ is an offset that is applied (step 280) to the set point of the column temperature of the LC system that is to perform the transferred chromatographic method.

Figure 5:
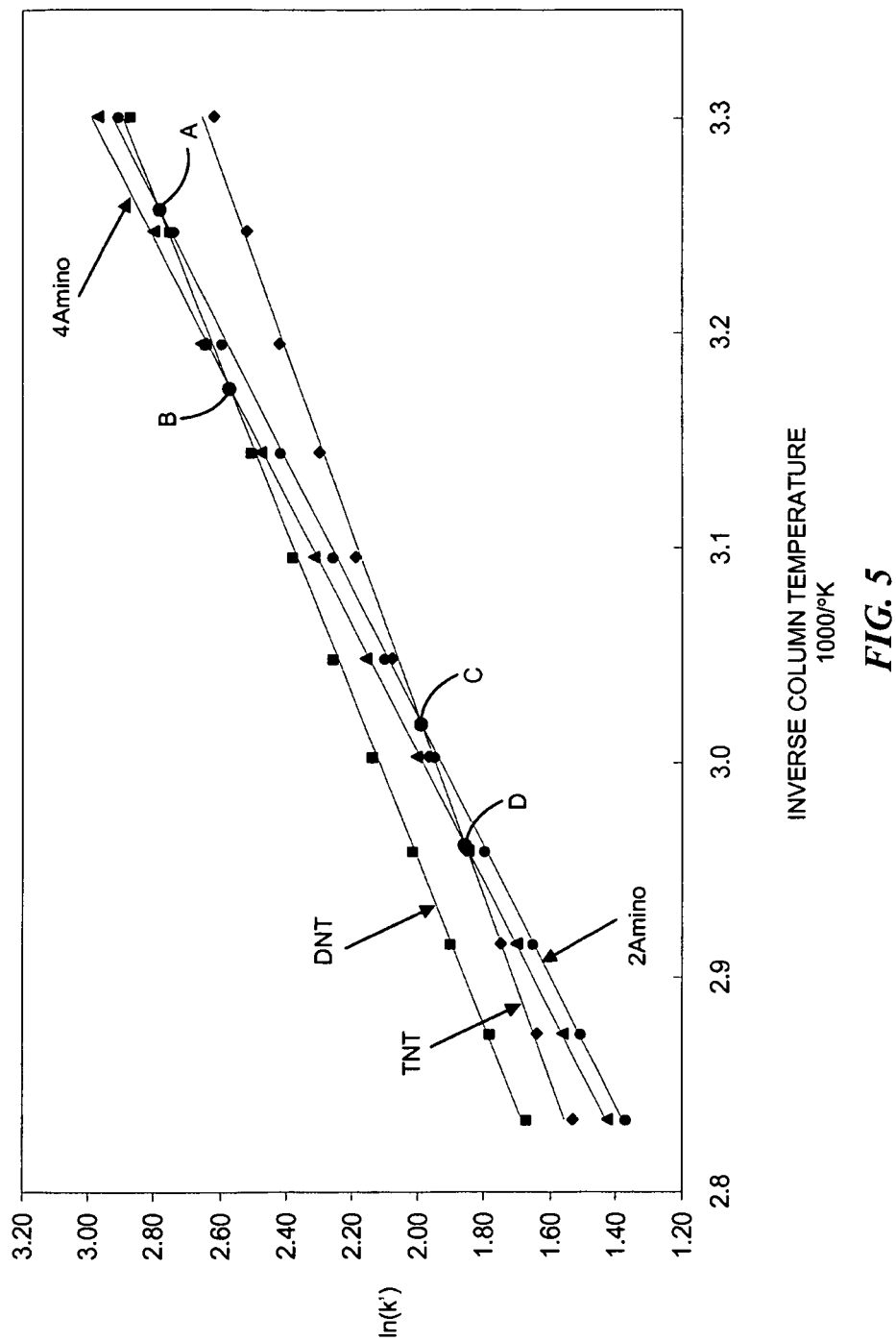
FIG. 5 graphically illustrates plots based on the van't Hoff equation for the four solutes of FIG. 3.

The method 200 can be applied to other pairs of solvents to determine other isoretention temperatures. For example, FIG. 5 graphically depicts the van't Hoff functional relationships for the four solutes of FIG. 3. The four isoretention temperatures 31.4° C., 41.7° C., 57.5° C. and 63.9° C. are determined from the four points A, B, C and D, respectively, at which the linear plots for two solutes intersect. It should be noted that that the graphical data in FIGS. 3 and 5 are mathematically related, that is, the data shown in FIG. 3 can be derived from the data of FIG. 5 and, conversely, the data shown in FIG. 5 can be derived from the data of FIG. 3. The van't Hoff plots of FIG. 5 enable linear interpolation to be used to accurately determine the four isoretention temperatures for the four solute pairs.

Preferably, when transferring a chromatographic method from between two LC systems, the isoretention temperatures for both LC systems for a common solute pair that are closest to the desired column temperature for the separation to be performed are used to determine the difference $\Delta T_{ISO}$. The difference $\Delta T_{ISO}$ is applied as an offset for the column set temperature of the LC system relative to the column set temperature used with the other LC system.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of transferring a chromatographic method between liquid chromatography (LC) systems, the method comprising:
    determining an isoretention temperature of a first LC system at which a first solute and a second solute in a mobile phase of the first LC system co-elute from a column;
    determining an isoretention temperature of a second LC system at which the first solute and the second solute in a mobile phase of the second LC system co-elute from a column; and
    determining a column offset temperature for transferring a chromatographic method between the first and second LC systems based on the difference in the isoretention temperatures of the first and second LC systems.

2. The method of claim 1 further comprising controlling a column temperature for a column in the first LC system in response to the column offset temperature.

3. The method of claim 2 further comprising:
    performing a separation on a sample using the first LC system at a first column temperature; and
    comparing results of the separation with results of a separation performed on the second LC system at a second column temperature, wherein a difference of the first and second column temperatures is equal to the column offset temperature.

4. The method of claim 1 wherein one of the first and second LC systems is a high-performance liquid chromatography (HPLC) system and the other of the first and second LC systems is a UPLC system.

5. The method of claim 1 wherein the column of the first LC system and the column of the second LC system are identical columns.

6. The method of claim 1 wherein the mobile phases of the first and second LC systems are identical mobile phases.

7. The method of claim 1 wherein a column of each of the first and second LC systems has a thermal gradient and wherein the first and second isoretention temperatures are average internal column temperatures.

8. The method of claim 1 wherein the steps of determining an isoretention temperature of a first LC system, determining an isoretention temperature of a second LC system and determining a column offset temperature are repeated one or more times to thereby determine a plurality of column offset temperatures.

9. The method of claim 8 further comprising:
    performing a separation on the first LC system at a first column temperature; and
    comparing results of the separation with results of a separation performed on the second LC system at a second column temperature, wherein a difference of the first and second column temperatures is equal to the column offset temperature.

10. A method of transferring a chromatographic method between liquid chromatography (LC) systems, the method comprising:
    determining, for a plurality of solute pairs each having a first solute and a second solute, an isoretention temperature of a first LC system at which the first solute and the second solute in a mobile phase of the first LC system co-elute from a column;
    determining, for each of the solute pairs, an isoretention temperature of a second LC system at which the first solute and the second solute in a mobile phase of the second LC system co-elute from a column; and
    determining, for each of the solute pairs, a column offset temperature for transferring a chromatographic method between the first and second LC systems based on the difference in a respective pair of isoretention temperatures of the first and second LC systems.

11. The method of claim 10 further comprising controlling a column temperature for a column in the first LC system in response to one of the column offset temperatures.

12. The method of claim 10 further comprising:
    performing a separation on a sample using the first LC system at a first column temperature; and
    comparing results of the separation with results of a separation performed on the second LC system at a second column temperature, wherein a difference of the first and second column temperatures is equal to one of the column offset temperatures.

13. The method of claim 12 wherein the difference of the first and second column temperatures is equal to the column offset temperature based on the isoretention temperatures of the first and second LC systems that are closest in value to at least one of the first column temperature and the second column temperature.

14. A method of transferring a chromatographic method between liquid chromatography (LC) systems, the method comprising:
    determining a van't Hoff functional relationship for a first solute in a mobile phase for a plurality of column temperatures for a first LC system;
    determining a van't Hoff functional relationship for a second solute in a mobile phase for a plurality of column temperatures for the first LC system;
    determining an isoretention temperature of the first LC system for the first and second solutes as a temperature at which a retention factor of each of the van't Hoff functional relationships of the two solutes in the first LC system are equal;
    determining a van't Hoff functional relationship for the first solute in a mobile phase for a plurality of column temperatures for a second LC system;
    determining a van't Hoff functional relationship for the second solute in a mobile phase for a plurality of column temperatures for the second LC system;
    determining an isoretention temperature of the second LC system for the first and second solutes as a temperature at which a retention factor of each of the van't Hoff functional relationships of the two solutes in the second LC system are equal; and
    determining a column offset temperature for transferring a chromatographic method between the first and second LC systems based on the difference in the isoretention temperatures of the first and second LC systems.

15. The method of claim 14 further comprising controlling a column temperature for a column in the first LC system in response to the column offset temperature.

16. The method of claim 15 further comprising:
    performing a separation on a sample using the first LC system at a first column temperature; and comparing results of the separation with results of a separation performed on the second LC system at a second column temperature, wherein a difference of the first and second column temperatures is equal to the column offset temperature.

17. A method of transferring a chromatographic method between liquid chromatography (LC) systems, the method comprising:
- determining, for a plurality of first solutes, a van't Hoff functional relationship for the first solute in a mobile phase for a plurality of column temperatures for a first LC system;
- determining, for a plurality of second solutes, a van't Hoff functional relationship for the second solute in a mobile phase for a plurality of column temperatures for the first LC system;
- determining, for a plurality of solute pairs each comprising one of the first solutes and one of the second solutes, an isoretention temperature of the first LC system as a temperature at which a retention factor of the van't Hoff functional relationships of the first and second solutes in the first LC system are equal;
- determining, for the plurality of first solutes, a van't Hoff functional relationship for the first solute in a mobile phase for a plurality of column temperatures for a second LC system;
- determining, for the plurality of second solutes, a van't Hoff functional relationship for the second solute in a mobile phase for a plurality of column temperatures for the second LC system;
- determining, for the plurality of solute pairs, an isoretention temperature of the second LC system as a temperature at which the retention factor of the van't Hoff functional relationships of the first and second solutes in the second LC system are equal; and
- determining, for each of the solute pairs, a column offset temperature for transferring a chromatographic method between the first and second LC systems based on a difference in a respective pair of isoretention temperatures of the first and second LC systems.

18. The method of claim 17 further comprising controlling a column temperature for a column in the first LC system in response to one of the column offset temperatures.

19. The method of claim 17 further comprising:
- performing a separation on a sample using the first LC system at a first column temperature; and
- comparing results of the separation with results of a separation performed on the second LC system at a second column temperature, wherein a difference of the first and second column temperatures is equal to one of the column offset temperatures.

* * * * *

UNITED STATES PATENT AND TRADEMARK OFFICE
CERTIFICATE OF CORRECTION

PATENT NO.         : 9,086,424 B2  
APPLICATION NO.    : 13/519712  
DATED              : July 21, 2015  
INVENTOR(S)        : Richard W. Andrews and Peyton C. Beals Page 1 of 1

It is certified that error appears in the above-identified patent and that said Letters Patent is hereby corrected as shown below:

Title Page Item (75), line 2,
- Replace the city "Wreatham" with the city "Wrentham"

Signed and Sealed this
Twenty-second Day of March, 2016

Michelle K. Lee
*Director of the United States Patent and Trademark Office*